US00PP24648P3

(12) United States Plant Patent
Berlin

(10) Patent No.: US PP24,648 P3
(45) Date of Patent: Jul. 15, 2014

(54) ***DRACAENA* PLANT NAMED 'MASS COAST'**

(50) Latin Name: *Dracaena fragrans steudnerii*
Varietal Denomination: Mass Coast

(76) Inventor: Erick Berlin, La Alegria (CR)

( * ) Notice: Subject to any disclaimer, the term of this patent is extended or adjusted under 35 U.S.C. 154(b) by 74 days.

(21) Appl. No.: 13/573,425

(22) Filed: Sep. 14, 2012

(65) Prior Publication Data

US 2014/0082800 P1 Mar. 20, 2014

(51) Int. Cl.
*A01H 5/00* (2006.01)

(52) U.S. Cl.
USPC ..... Plt./383

(58) Field of Classification Search
USPC ..... Plt./383
See application file for complete search history.

*Primary Examiner* — Kent L Bell
(74) *Attorney, Agent, or Firm* — Cassandra Bright

(57) ABSTRACT

A new and distinct *Dracaena* cultivar named 'Mass Coast' is disclosed, characterized by dark green leaves with a strong yellow-green center stripe. Plants produce thick stems, which color early. The new variety is a *Dracaena*, typically produced as an ornamental plant.

1 Drawing Sheet

Latin name of the genus and species: *Dracaena fragrans steudnerii.*

Variety denomination: 'Mass Coast'.

BACKGROUND OF THE INVENTION

The new cultivar is the product of chance discovery. The new variety originated as a naturally occurring, whole plant mutation of an unpatented, unnamed variety of *Dracaena fragrans steudnerii.*

The new variety was discovered by the inventor, Erick Berlin, a citizen of the United States, in 2006 in a commercial nursery in Porton de Iberia, Costa Rica. After identifying the new variety as a potentially interesting selection, the inventor continued confidential testing and propagation of 'Mass Coast', assessing the stability of the unique characteristics of this variety.

Asexual reproduction of the new cultivar 'Mass Coast' was first performed at the commercial nursery in Porton de Iberia, Costa Rica by vegetative cuttings in 2006. Access to all plants was restricted, as plants were kept in an area not open to the public. The inventor has filed an application in the EU, 2009/1104, with grant number EU30634, filed Jun. 15, 2009. During the application process in the EU, plants were not available to the public, and sales had not been made. First sales of 'Mass Coast' were November, 2011. Propagation of *Dracaena* varieties requires a long period of time to build up motherstock plants. The inventor developed his own restricted stock of mother plants, meanwhile, continuing to assess the stability of the foliage variegation of the new variety. Through subsequent propagation by vegetative cuttings, multiple generations have been reproduced, which have shown that the unique features of this cultivar are stable and reproduced true to type.

SUMMARY OF THE INVENTION

The cultivar 'Mass Coast' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Mass Coast'. These characteristics in combination distinguish 'Mass Coast' as a new and distinct *Dracaena* cultivar:

1. Thick stem.
2. Early coloration of the stem.
3. Distinctive dark green foliage with a yellow-green center stripe.

PARENT COMPARISON

Plants of the new cultivar 'Mass Coast' are similar to the parent, an unpatented, unnamed variety of *Dracaena fragrans steudnerii* in most horticultural characteristics. The new variety, however, produces dark green foliage with a strong yellow center stripes, whereas the parent variety produces solid dark green foliage.

COMMERCIAL COMPARISON

'Mass Coast' is similar to the unpatented commercial variety *Dracaena fragrans* 'Massangeana' in most horticultural characteristics. The new variety, however, produces leaves that are shorter, and narrower than 'Massangeana'. Additionally, the two varieties vary somewhat in foliage color.

'Mass Coast' is similar to the unpatented commercial variety *Dracaena fragrans steudneri* 'Cintho' in most horticultural characteristics. The new variety, however, produces leaves that are shorter, and broader than 'Cintho'. Plants of 'Mass Coast' have a thicker stem, which colors earlier than the stem produced by plants of 'Cintho'. Additionally, the two varieties vary somewhat in foliage color.

BRIEF DESCRIPTION OF THE PHOTOGRAPH

The accompanying photograph in FIG. 1 illustrates in full color a typical plant of 'Mass Coast' grown in a commercial greenhouse in Munster, The Netherlands. This plant is approximately 15 weeks old, shown planted in a 10.5 cm container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'Mass Coast' plants grown in a greenhouse in Munster, The Netherlands. A steady temperature of approximately 20° C. at night and 20° C. during the day was maintained. No artificial light, photoperiodic treatments were given to the plants. The plant was shaded if the sun was shining on it. Measurements and numerical values represent averages of typical plant types.

Botanical classification: *Dracaena fragrans steudnerii* 'Mass Coast'.

PROPAGATION

Time to initiate rooting: About 4 to 5 weeks at approximately 20° C.

Root description: Moderately thick, moderately fibrous, not fleshy, young roots Yellow-White 158D, older roots Greyed-Orange 163C.

PLANT

Age of plant described: 15 weeks.
Pot size of plant described: 10.5 cm circular pot.
Growth habit: Upright.
Height: Approximately 49.5 cm.
Plant spread: Approximately 38.5 cm.
Growth rate: Moderate, approximately 8 cm per month.
Branching characteristics: Not free branching, growing with one main stem from the base, from which two lateral stems grow after being pinched. Will only develop lateral branches after pinching or pruning.
Diameter of stem: Old stem approximately 3.0 cm, younger, lateral stems, arising from a pinch average 0.9 cm.
Internode length: Average 1.6 cm.
Texture of stem: Smooth, dull, young stems slightly glossy.
Color of stem: Green and yellow-green, near RHS 143B and 145B.
Stem strength: Very strong.
Number of leaves per stem: Average 13.

FOLIAGE

Leaf:
- *Arrangement*.—Alternate (spirally).
- *Average length*.—Approximately 27.6 cm.
- *Average width*.—Approximately 5.9 cm.
- *Shape of blade*.—Lorate.
- *Aspect*.—Slight undulation, more pronounced at margins.
- *Angle*.—Leaves in an average angle of 35° to lateral stems.
- *Apex*.—Long acuminate, slightly pointed downwards in an average angle of 30° to leaf blade (=0°), not sharp.
- *Base*.—Broad cuneate.
- *Attachment*.—Sheathing.
- *Margin*.—Entire.
- *Texture of top surface*.—Smooth, glossy.
- *Texture of bottom surface*.—Smooth, slightly glossy.

Color:
- *Young foliage upper side*.—Green to yellow-green; a color between RHS 143A and 144A but slightly darker, center striped (axial) yellow-green; near 144A, 144B and 144C.
- *Young foliage under side*.—Green; a color in between RHS 138A and 144A, center striped (axial) yellow-green; near 144B.
- *Mature foliage upper side*.—Green to yellow-green; near in between RHS N137A and 144A but much darker, center striped (axial) yellow-green; near 144A and N144A.
- *Mature foliage under side*.—Green to yellow-green; near in between RHS 137B and 146A, center striped (axial) yellow-green; near 145A and 150C.

Venation:
- *Type*.—Parallel.
- *Color*.—Upperside: Indistinguishable from leaf blade. Underside: Main vein yellow-green; near RHS 151C, other veins colored as leaf blade.

Sheath:
- *Average length*.—Approximately 2.0 cm.
- *Average Width*.—Approximately 1.2 cm.
- *Color*.—Central part yellow-green; near RHS 145D, margins near RHS 148B.
- *Texture*.—Smooth, glossy.

OTHER CHARACTERISTICS

Flower production: Not observed.
Disease resistance: Neither resistance nor susceptibility to normal diseases and pests of *Dracaena* has been observed.
Drought tolerance and temperature tolerance: Moderately high drought resistance, good heat resistance to at least 40° C.
Fruit/seed production: Not observed.

What is claimed is:

1. A new and distinct cultivar of *Dracaena* plant named 'Mass Coast' as herein illustrated and described.

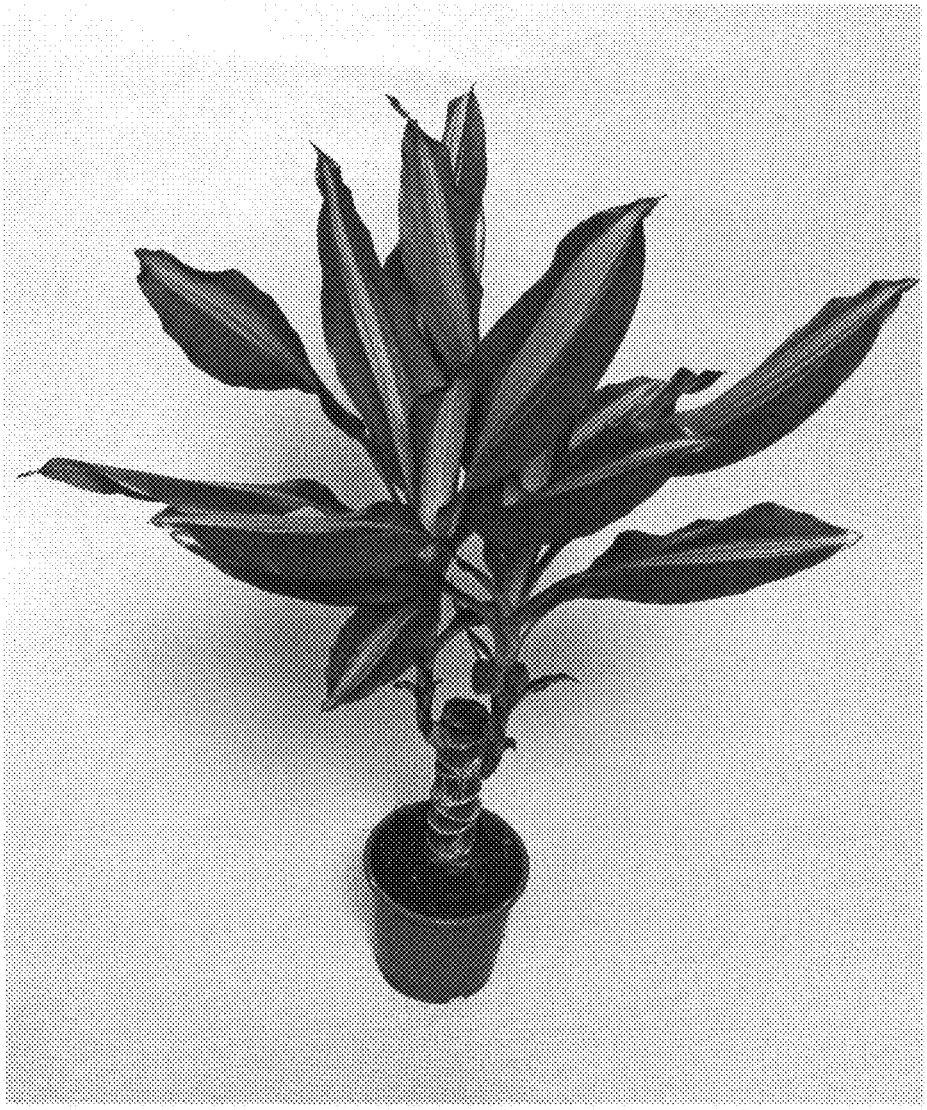

* * * * *